United States Patent [19]

Hu

[11] Patent Number: 5,916,265
[45] Date of Patent: Jun. 29, 1999

[54] METHOD OF PRODUCING A BIOLOGICAL EXTRACELLULAR MATRIX FOR USE AS A CELL SEEDING SCAFFOLD AND IMPLANT

[76] Inventor: Jie Hu, 1752 Ashley Hall Rd., Charleston, S.C. 29407

[21] Appl. No.: 08/468,270

[22] Filed: Jun. 6, 1995

Related U.S. Application Data

[63] Continuation-in-part of application No. 08/219,960, Mar. 30, 1994, abandoned.

[51] Int. Cl.[6] ........................................................ A61F 2/02
[52] U.S. Cl. .......................... 623/11; 623/1.6; 128/DIG. 8
[58] Field of Search .................. 623/11, 1.6; 128/DIG. 8

[56] References Cited

U.S. PATENT DOCUMENTS

| | | | |
|---|---|---|---|
| 4,801,299 | 1/1989 | Brendel et al. | 623/1 |
| 4,969,912 | 11/1990 | Kelman et al. | 623/66 |
| 5,112,354 | 5/1992 | Sires | 623/16 |

FOREIGN PATENT DOCUMENTS 564786  10/1993  European Pat. Off. .

OTHER PUBLICATIONS

Osamu Ohtani Three dimensional Organization of the Connective Tissue Fibers of the Human Pancreas: A Scanning electron Microscopic Study of NaOH treated tissues vol. 5 pp. 557–566.

O'Donnel et al: An alkali Digestion method to expose connective Tissue Fibers: A Scanning electron Microscopic Study of Rat lung (Journal of Electron Microscopy technique 19: 486–496 (1991).

Schneider et al: An improved method for endothelid cell seeding on polytetrafluoroethylene small caliber vascular grafts.

*Primary Examiner*—Duc Truong

[57] ABSTRACT

Tissue is procured from a human or animal donor. The tissue may be fixed by application of a fixative. Cellular components which would cause rejection are removed from tissue by a chemical treatment that allows the extracellular matrices (ECM) to retain their original shapes, biological structures and ultrastructures, locations and durability. The resulting ECM serves as a cell scaffold on which living cells are seeded to form a lifegraft for implanting or for allograft reconstruction.

21 Claims, No Drawings

METHOD OF PRODUCING A BIOLOGICAL EXTRACELLULAR MATRIX FOR USE AS A CELL SEEDING SCAFFOLD AND IMPLANT

This application is a continuation-in-part of application Ser. No. 08/219,960 filed Mar. 30, 1994, now abandoned.

FIELD OF THE INVENTION

This invention relates to a method of producing a biological extracellular matrix produced from tissue harvested or procured from human or animal tissue.

BACKGROUND OF THE INVENTION

The loss or failure of an organ or tissue is one of the most frequent, devastating, and costly problems in human health care. A new field, tissue engineering, applies the principles of biology and engineering to the development of functional substitutes for damaged tissue.

Tissue engineering is an interdisciplinary field that applies the principles of engineering and the life sciences toward the fundamental understanding of structure-function relationships in normal and pathological mammalian tissue and the development of biological substitutes that restore, maintain, or improve tissue function. It involves the use of living cells, together with extracellular matrices, either natural or synthetic, in the development of implantable parts or devices for the restoration or replacement of function.

One of the three general strategies that have been adopted for the creation of new tissue substitutes is the utilization of cells placed on or within matrices. The matrices are fashioned from natural materials, or from synthetic biodegradable polymer fiber scaffolds, and are then used as the ECM.

Despite the evolution of numerous artificial or synthetic grafts that have been developed, these tissue replacements are still unable to adequately substitute for nature's highly complex structures. Today's challenge in tissue transplantation is to overcome the body's defense system and to strive to improve the functioning of the graft. Despite major advancements in this field, modern tissue transplantation remains associated with complications including inflammation, degradation, scarring, contracture, calcification (hardening), occlusion and rejection. There have been extensive medical biomaterial research efforts directed toward the engineering of improved transplantable tissue grafts, however an ideal artificial graft has not yet been developed.

Detergents have been used in the prior art to remove cellular components from tissue, as described in Brendel. et. al., U.S. Pat. No. 4,801,299. However, as described therein, the detergents cannot be successfully used with tissues which have previously been altered with a fixative, such as a crosslinking agent.

SUMMARY OF THE INVENTION

An objective of this invention is to provide a method of processing biological tissue by chemical treatment for the production of a decellularized collagen-based extracellular matrix (ECM) derived from humans and animals for transplantation into humans or animals. This invention provides an efficient method of producing an improved ECM generally having the original shape of the tissue while also retaining the desired biological structure. The tissue may be harvested or procured by known methods. The tissue may be autologous or obtained from cadavers or from donors. The tissue may be decellularized after the application of a fixative.

After the tissue is procured, a fixative is applied to the tissue. An hydroxide solution, such as sodium hydroxide or potassium hydroxide, is applied. The ECM so produced is then washed, and incubated, and may be stored.

As a cell scaffold, this ECM can be seeded with cells that are derived from the host (autologous cells) or from an alternative human source before transplantation. This ECM from body tissue may also allow the use of such matrix materials for tissue replacement.

DESCRIPTION OF THE PREFERRED EMBODIMENT

The present invention involves the procurement of a section of biological tissue through the steps of fixed treatment and cell removal, sterilization and cellular reconstitution, to provide a biological tissue replacement for transplantation.

In the preferred embodiment, the tissue which is procured is preferably the same as the tissue in which grafts are to be subsequently implanted. For example, skin is used to replace skin, arteries are used to replace arteries, veins are used to replacing veins, and cartilage is used to replace cartilage.

Biological tissue from a human, cadaver or animal donor is procured or harvested with a volume of $1 \times 1 \times (1 \ldots n)$ one cubic centimeter or larger, and is immediately placed in a fixative solution with a crosslinking agent, such as glutaraldehyde or formaldehyde. The fixative solution may comprise 2% paraformaldehyde and 1.5% glutaraldehyde in sodium phosphate buffer (PBS) solution. The tissue remains in the fixative for a minimum time of approximately 2 hours, or until the tissue is completely fixed. After the tissue is fixed, several washings with an appropriate material, such as with distilled water, are performed.

In the preferred embodiment, the tissue is then placed in a sodium hydroxide or potassium hydroxide solution, or any other alkali group solution comprising a hydroxyl group, for incubation of the tissue to remove cells from the fixed tissue. The tissue remains in this solution for a period ranging from about from 2 hours to 5 days, at room temperature. A solution comprising 1.5–2.0N $N_a$OH or KOH is preferred. The concentration may range from 0.1N to 5N, and the temperature may range from about 4° C. to 60° C., depending on the type of donor tissue processed, and the length of time required to obtain the decellularized ECM. Higher concentrations, higher temperature or longer digestion will tend to diminish the results. In practice, prolonged treatment with $N_a$OH or KOH at room temperature resulted in the digestion of elastic fibers. The resulting ECM may be observed by light and scanning electron microscopy.

After the tissue is decellularized, washing of the tissue is performed. The solution with which the tissue is washed may be distilled water and a buffer, such as sodium phosphate. In this step, the washing solution is changed, preferably about every 30 minutes, and washing continues until the ECM is semitransparent in appearance. After the ECM is washed, the ECM is incubated in an amino acid such as aspartic acid, glutamic acid, or glycine solution, to eliminate residual free crosslinking solution, and to the reduce the pH. The particular amino acids could be 0.5% aspartic acid, or 0.1M glycine solution. Incubation of the ECM in a buffer solution will ultimately bring the pH of the wash solution to about 7.4. After processing, the decellularized ECM can be placed and stored in any manner which will not damage the ECM structure prior to transplantation or implantation.

The ECM structure provides a suitable and efficient biosubstrate for cell adhesion, growth, and differentiation.

This ECM can be used as cell scaffold seeding living cells onto it to become a tissue replacement by in vitro cell culturing techniques prior to transplantation, or it may directly become a structure template to be implanted internally in the body, or externally on the body, by a variety of medical procedures. The ECM may be used to form an autograft or an allograft.

This invention produces a tissue product comprising a well preserved ECM. This ECM plays an active and complex role in regulating the behavior of the cells that come in contact with it. In fact, although the extracellular matrix (ECM) that lies under epithelia and surrounds connective tissue cells is a relatively stable structural material, the idea that the ECM is an inert supporting material, created by the cells as a mere scaffolding on or in which to reside, is now bygone. Each of the isolated constituents of the ECM has a special function, and combines to form a three dimensional structure surrounding the cells and collagens which is a source of strength to the tissue, elastin and proteoglycans which are essential to matrix resiliency, and the structural glycoproteins which help to create extracellular macromolecules, and having influenced their assembly, do not then divorce themselves from the structure. The cells continue to interact with their own ECM products, and with the ECM produced by other cells. At the cell surface, matrix receptors link the ECM to the cell interior, and the metabolism and fate of the cell, its shape, and many of its other properties are continuously related to and dependant upon the composition and organization of the matrix. In this specifically treated biological tissue, all cellular components which normally express major histocompatibility complex antigenic determinants and other antigens which would be recognized as foreign by the recipient and cause rejection are removed. The preserved ECM product is contracted from biological tissue which retains its original shape, biologic structure, ultrastructure, location and durability as the ECM produced from the tissue.

Because this intact, naturally produced ECM, when compared with presently commercial available implants, has a natural biological architecture which is difficult to imitate, an ECM is produced having superior performance in most applications. This ECM is absolutely nontoxic, causes no adverse allergenic activity and works to promote cell proliferation, when compared with implants which are comprised of chemical polymer substrates coated with ECM components such as like collagen or fibronectin. When the present invention is compared with the ECM and method of Brendel. et al., U.S. Pat. No. 4,801,299, this innovative technological method is more effective, and produces an ECM by an easier, simpler, and less expensive method in a much shorter time, while keeping the natural structure intact as required.

What is claimed is:

1. A method of preparing biological implants by removing cellular components and forming an extracellular matrix, comprising the steps of:
   a. procuring tissue;
   b. fixing said tissue by application of a cross linking agent; and
   c. subsequently decellularizing said tissue by applying a solution comprising a compound having a hydroxyl group to said tissue.

2. A method of preparing biological implants by removing cellular components and forming an extracellular matrix as described in claim 1, further comprising a step of washing the tissue with a buffer solution.

3. A method of procuring biological implants by removing cellular components and forming an extracellular matrix as described in claim 2, further comprising the steps of incubating said extracellular matrix in an incubation solution, eliminating residual free crosslinking solution and reducing the alkalinity of said extracellular matrix.

4. A method of procuring biological implants by removing cellular components and forming an extracellular matrix as described in claim 3, wherein said incubation solution is aspartic acid.

5. A method of procuring biological implants by removing cellular components and forming an extracellular matrix as described in claim 3, wherein said incubation solution is glutamic acid.

6. A method of procuring biological implants by removing cellular components and forming an extracellular matrix as described in claim 3, wherein said incubation solution is a glycine solution.

7. A method of preparing biological implants by removing cellular components and forming an extracellular matrix, comprising the steps of:
   a. procuring tissue;
   b. fixing said tissue by application of a cross linking agent;
   c. subsequently decellularizing said tissue by applying a solution comprising a compound having a hydroxyl group to said tissue; and
   d. seeding said tissue with living cells to form a graft.

8. A method of preparing biological implants by removing cellular components and forming an extracellular matrix as described in claim 7, further comprising a step of washing the tissue with a buffer solution prior to seeding the tissue with living cells.

9. A method of procuring biological implants by removing cellular components and forming an extracellular matrix as described in claim 8, further comprising the steps of incubating said extracellular matrix in an incubation solution, eliminating residual free crosslinking solution and reducing the alkalinity of said extracellular matrix prior to seeding the tissue with living cells.

10. A biological extracellular matrix for use in grafting produced by a method comprising the steps of:
    a. procuring a section of biological tissue;
    b. preserving the biological components and structures of the section of biological tissue by fixing said section of biological tissue by means of application of a cross linking agent;
    c. applying an alkali solution comprising a compound having a hydroxyl group to said section of biological tissue;
    d. applying an additional solution to the section of biological tissue to remove residual cross linking agent from the tissue; and
    e. washing the section of biological tissue with a buffer solution to neutralize the pH of said section of biological tissue.

11. A biological extracellular matrix for use in grafting produced by the method described in claim 10 further comprising the step of seeding living cells onto said section of biological tissue after said section of biological tissue is washed with said buffer solution.

12. A biological extracellular matrix produced by the method described in claim 10, further comprising the step of implanting said section of biological tissue as an extracellular matrix.

13. A biological extracellular matrix produced by the method described in claim 10, wherein said additional solution is changed periodically until the biological extracellular matrix is semi-transparent and the pH of the solution is about 7.4.

14. A biological extracellular matrix produced by the method described in claim 1, wherein the solution is a sodium hydroxide solution.

15. A biological extracellular matrix produced by the method described in claim 10, wherein the solution is a sodium hydroxide solution.

16. A biological extracellular matrix produced by the method described in claim 11, wherein the solution is a sodium hydroxide solution.

17. A biological extracellular matrix produced by the method described in claim 12, wherein the solution is a sodium hydroxide solution.

18. A biological extracellular matrix produced by the method described in claim 1, wherein the solution is a potassium hydroxide solution.

19. A biological extracellular matrix produced by the method described in claim 10, wherein the solution is a potassium hydroxide solution.

20. A biological extracellular matrix produced by the method described in claim 11, wherein the solution is a potassium hydroxide solution.

21. A biological extracellular matrix produced by the method described in claim 12, wherein the solution is a potassium hydroxide solution.

* * * * *